United States Patent [19]

Jack et al.

[11] Patent Number: 5,591,975

[45] Date of Patent: *Jan. 7, 1997

[54] OPTICAL SENSING APPARATUS FOR REMOTELY MEASURING EXHAUST GAS COMPOSITION OF MOVING MOTOR VEHICLES

[75] Inventors: Michael D. Jack, Goleta, Calif.; Robert D. Stephens, Sterling Heights, Mich.; Christopher B. Tacelli, Goleta, Calif.; David R. Nelson, Santa Barbara, Calif.; Geoffrey A. Walter; Jose A. Santana, both of Goleta, Calif.; Lane H. Rubin, Santa Barbara, Calif.

[73] Assignee: Santa Barbara Research Center, Goleta, Calif.

[*] Notice: The term of this patent shall not extend beyond the expiration date of Pat. No. 5,418,366.

[21] Appl. No.: 318,566

[22] Filed: Oct. 5, 1994

Related U.S. Application Data

[63] Continuation-in-part of Ser. No. 119,788, Sep. 10, 1993, abandoned, and Ser. No. 239,151, May 5, 1994, Pat. No. 5,418,366.

[51] Int. Cl.$^6$ .......................... G01N 21/25; G01N 21/35
[52] U.S. Cl. ..................... 250/338.5; 250/338.5; 250/339.12; 250/339.13; 356/436; 356/438
[58] Field of Search ................................. 250/343, 345, 250/338.5, 339.12, 339.13; 356/436, 437, 438

[56] References Cited

U.S. PATENT DOCUMENTS

| | | |
|---|---|---|
| 3,696,247 | 11/1972 | McIntosh et al. |
| 3,973,118 | 8/1976 | LaMontagne |
| 4,204,768 | 5/1980 | N'Guyen |
| 4,560,873 | 12/1985 | McGowan et al. |
| 4,632,563 | 12/1986 | Lord, III |

(List continued on next page.)

FOREIGN PATENT DOCUMENTS 1-320438  12/1989  Japan.

OTHER PUBLICATIONS

Stedman, Donald H. "Automobile carbon monoxide emission", 1989, Environ. Sci. Technol. vol. 23, No. 2, pp. 174–149.

Bishop, G. et al., "Analytical Approach —IR Long-Path Photometry: A Remote Sensing Tool for Automotive Emissions", Analytical Chemistry 1989, 61, 617A.

(List continued on next page.)

*Primary Examiner*—Constantine Hannaher
*Assistant Examiner*—Edward J. Glick
*Attorney, Agent, or Firm*—W. C. Schubert; W. K. Denson-Low

[57] ABSTRACT

A light source radiates an infrared beam that passes through a chopper, a calibration cell and the exhaust plume of a motor vehicle passing in front of the source. A photosensor assembly includes a plurality of photodetectors which are spaced closely adjacent to each other and simultaneously sense the beam after it propagates through the plume. An optical beam homogenizer or integrator disposed between the plume and the photosensor unit causes the light incident on the photodetectors to have uniform intensity. The photodetectors are sensitive to different wavelengths corresponding to spectral absorption peaks of constituents of the composition of the plume, including carbon monoxide (CO), carbon dioxide ($CO_2$), hydrocarbon (HC), water vapor ($H_2O$) and nitric oxide (NO). A computer computes the composition of the plume as the percentages of the constituents based on the sensed transmittances of the respective wavelengths through the plume. A video camera produces a video image of the vehicle license plate, which is displayed on a video monitor and recorded on a video recorder together with the plume composition data.

50 Claims, 12 Drawing Sheets

U.S. PATENT DOCUMENTS

| | | |
|---|---|---|
| 4,638,345 | 1/1987 | Elabd et al. . |
| 4,710,630 | 12/1987 | Kuppenheimier, Jr. et al . |
| 4,829,183 | 5/1989 | McCiatchie et al. ............... 250/345 X |
| 4,868,622 | 9/1989 | Shigenaka . |
| 4,875,084 | 10/1989 | Yohyama . |
| 4,924,095 | 5/1990 | Swanson, Jr. . |
| 5,041,723 | 8/1991 | Ishida et al. . |
| 5,157,258 | 10/1992 | Gunning, III et al. . |
| 5,185,648 | 2/1993 | Baker et al. . |
| 5,210,702 | 5/1993 | Bishop et al. . |
| 5,252,828 | 10/1993 | Kert et al. . |
| 5,254,858 | 10/1993 | Wolfman et al. . |
| 5,319,199 | 6/1994 | Stedman et al. . |
| 5,332,901 | 7/1994 | Eckles et al. . |
| 5,418,366 | 5/1995 | Rubin et al. .......................... 250/338.5 |

OTHER PUBLICATIONS

Stevens, R. K. and Teri L. Vossler, "DOAS urban pollution measurements", SPIE vol. 1433, Measurement of Atmospheric Gases, 1991, pp. 25–35.

Stephens, Robert D. and Steven H. Cadle, "Remote sensing measurements of carbon monoxide emissions from on-road vehicles", Jan. 1991, J. Air & Waste Manage, vol. 41, No. 1, pp. 39–46.

Chaney, Lucian W., "The remote measurement of traffic generated carbon monoxide", Mar. 1993, vol. 33, No. 3, J. Air Pollution Control Association, pp. 220–222.

Peterson, James E. et al., "Find and Fix the Polluters" Chemtech, Jan. 1992, pp. 47–53.

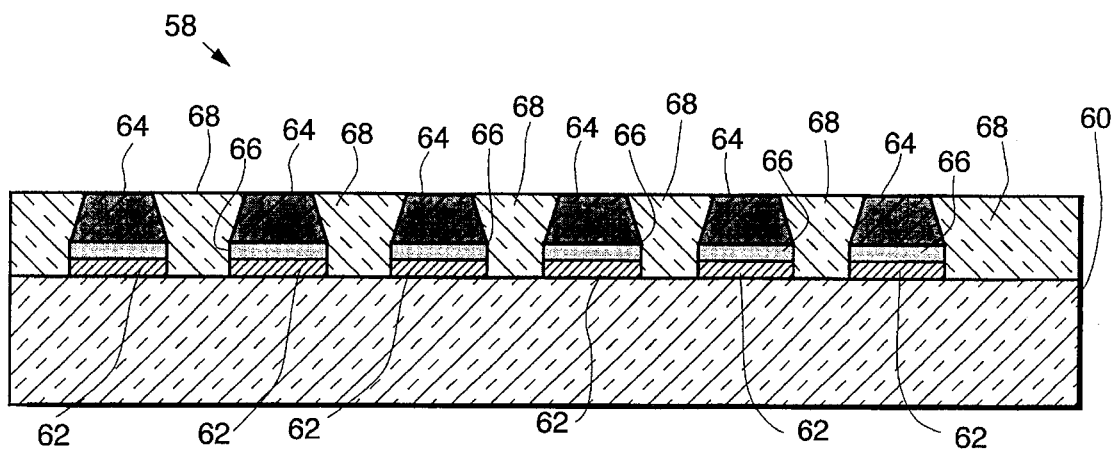
FIG. 6.
FIG. 7.
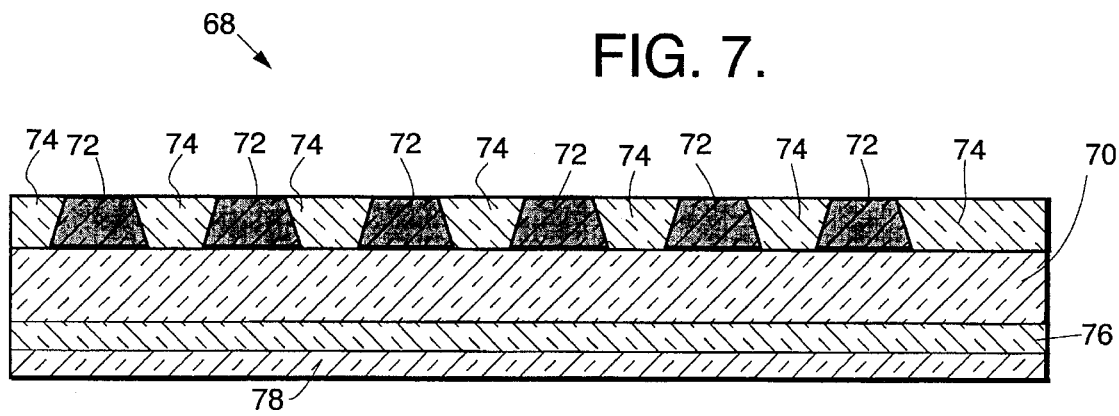

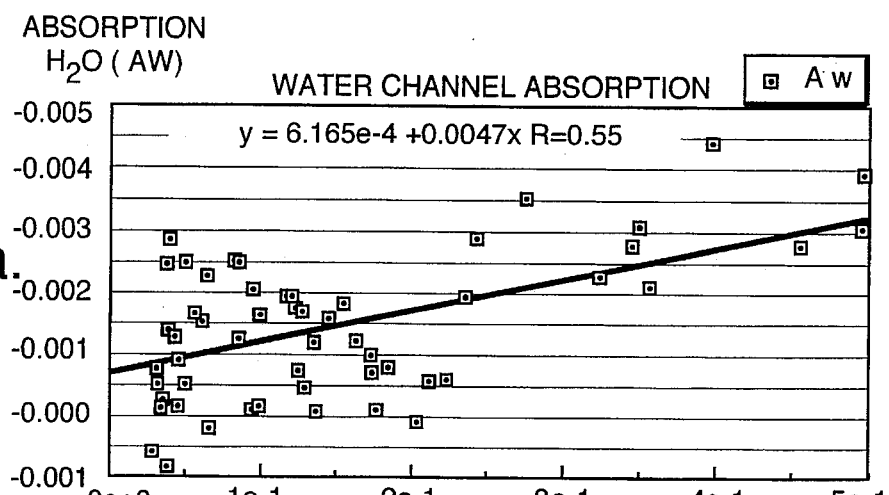
FIG.17a.
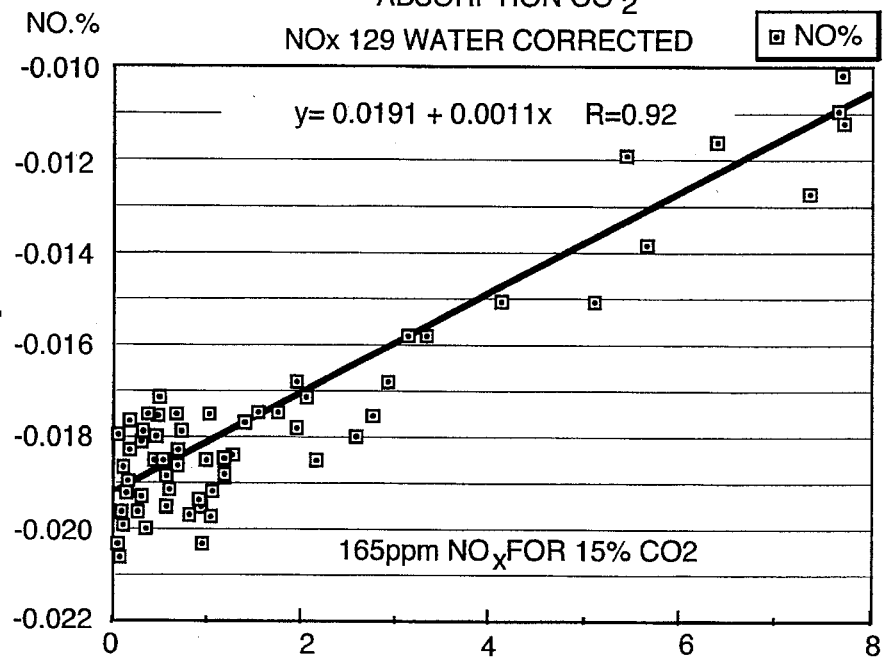
FIG.17b.
FIG.17c.

FIG. 18.
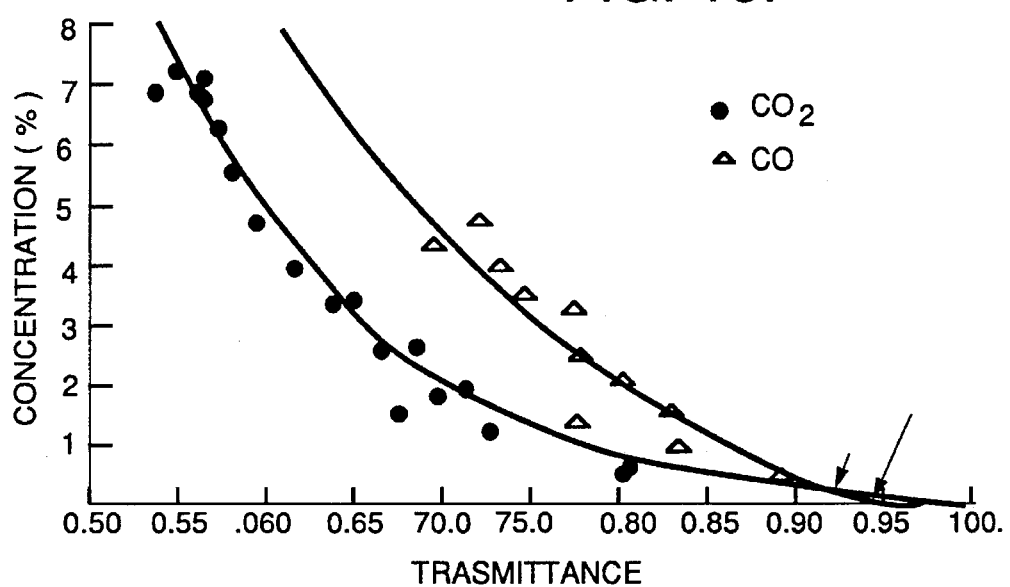
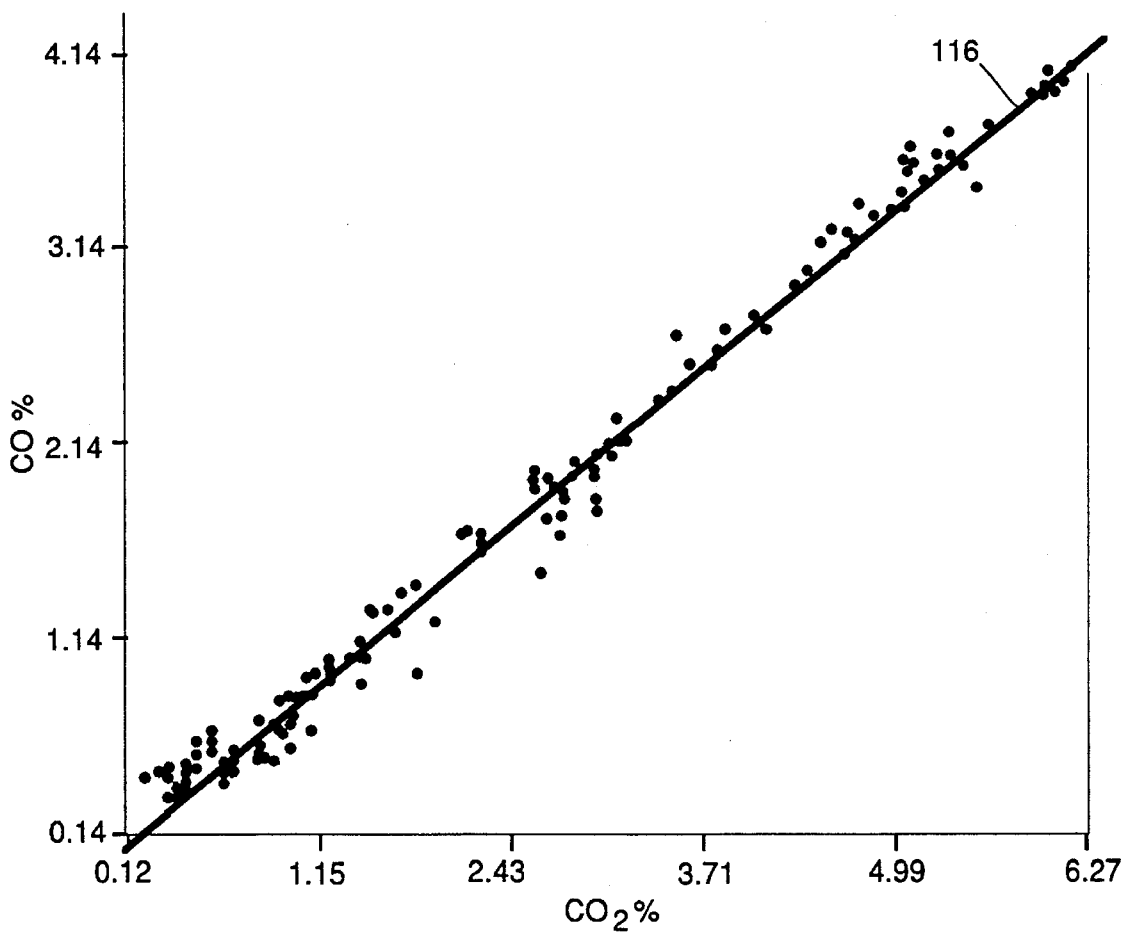
FIG. 19.

OPTICAL SENSING APPARATUS FOR REMOTELY MEASURING EXHAUST GAS COMPOSITION OF MOVING MOTOR VEHICLES

RELATED APPLICATIONS

This application is a continuation-in-part of application Ser. No. 08/119,788, filed Sep. 10, 1993, now abandoned, and continuation-in-part of application Ser. No. 08/239,151, filed May 5, 1994, now U.S. Pat. No. 5,418,366.

FIELD OF THE INVENTION

The present invention generally relates to the monitoring of environmental pollution, and more specifically to an optical sensing apparatus for remotely monitoring the exhaust gas composition of moving motor vehicles and emissions from industrial and other sources.

BACKGROUND OF THE INVENTION

Environmental pollution is a serious problem which is especially acute in urban areas. A major cause of this pollution is exhaust emissions from automotive vehicles. Official standards have been set for regulating the allowable amounts of pollutants species in automobile exhausts, and in some areas, periodic inspections or "smog checks" are required to ensure that vehicles meet these standards.

However, there are still large numbers of vehicles operating on public highways which fail to comply with the standards. It has also been determined that a disproportionately large amount of pollution is generated by a relatively small number of vehicles.

Highly polluting vehicles can operate even in areas in which periodic emission inspections are required. Some older vehicles and special types of vehicles are exempt from inspections.

Anti-pollution devices which are required equipment on newer vehicles accomplish their intended purpose of reducing pollution in the vehicle exhaust to within prescribed levels. However, it is perceived by some vehicle owners that antipollution equipment reduces engine performance.

For this reason, some vehicle owners with mechanical expertise can perform whatever servicing is necessary to place their vehicles in condition to pass required inspections, and subsequently remove anti-pollution devices and/or return the vehicles with an attendant increase in pollutant emissions for normal use.

An anti-pollution program which depends entirely on mandatory periodic inspections performed at fixed facilities is therefore inadequate. It is necessary to identify vehicles which are actually operating in violation of prescribed emission standards, and either require them to be placed in conformance with the standards or be removed from operation.

A system for remote sensing of automotive exhaust emissions is described in an article entitled "ANALYTICAL APPROACH—IR Long-Path Photometry: A Remote Sensing Tool for Automotive Emissions:, by G. Bishop et al., in Analytical Chemistry 1989, 61, 617A. An infrared beam is transmitted through the exhaust plume of an automotive vehicle to a sensor unit which includes a beam splitter which splits the beam into a carbon dioxide ($CO_2$) channel and a carbon monoxide (CO) channel.

The beam in the $CO_2$ channel passes through a bandpass filter which isolates the spectral absorption region of carbon dioxide and is incident on a photovoltaic detector. The beam in the CO channel passes through a rotating gas filter wheel, one-half of which contains a CO and hydrogen ($H_2$) mixture, and the other half of which contains nitrogen ($N_2$). From the filter wheel, the beam in the CO channel passes through another bandpass filter which isolates the spectral absorption region of carbon monoxide and is incident on another photovoltaic detector.

The output signals of the detectors vary in accordance with the transmittance of the vehicle exhaust plume at the respective wavelengths, and thereby the concentrations of CO and $CO_2$ in the plume. The $CO/H_2$ portion of the filter wheel provides a reference output, whereas the $N_2$ portion provides a carbon monoxide output.

Baseline sensor outputs are obtained with no vehicle passing through the beam, and with the beam blocked by a vehicle prior to sensing of the plume. These values are used as references for calibrating the outputs of the detectors when the plume is actually sensed. The detector outputs, which correspond to the transmittances at the respective wavelengths, are then processed in accordance with predetermined functions to determine the relative percentages of $CO_2$ and CO in the vehicle exhaust plume.

This system is said to be capable of sensing the exhaust gas composition of moving vehicles, and to be useful in identify polluting vehicles for enforcement purposes. However, it suffers from certain drawbacks.

For example, precise alignment is required to ensure that the beams in the two paths are incident on the detectors in an identical manner. A small misalignment error can seriously degrade the measurement accuracy. The two photovoltaic detectors are remote from each other, and require separate cooling units for temperature regulation. A small difference in temperature, as well as small mismatches in other characteristics of the detectors, can also seriously degrade the measurement accuracy.

The rotating filter wheel is a mechanical unit which is expensive and prone to mechanical malfunction. The concentrations of the gases in the filter must be maintained at precise values in order to obtain accurate measurements. The system is also difficult to expand for sensing of additional pollutant species, since each new channel will require another beam splitter, detector, etc. and involve the problems described above.

One particularly noxious pollutant that is not sensed at all by known types of systems, or that is only inaccurately sensed, is nitric oxide (NO). Standard infrared techniques such as FTIR fail in quantifying NO in the atmosphere because of the significant interference resulting from water absorption in absorbing bands in the region around 5.2 μm and 6.2 μm in which NO absorbs. Attempts to subtract the water absorption band are not successful due to the limited accuracy with which water absorption signature can be modeled over the entire spectral region in which FTIR, by its nature, must scan.

Alternate IR laser approaches that use overtone techniques are also not adequate, due at least in part to the requirement to compensate for the water vapor absorption, and to a requirement to provide very accurate temperature control.

An alternative approach utilizes UV absorption in the spectral region around 270 nm. Although NO absorption is strong in this spectral region, the application of this approach to moving vehicles is difficult due to interference from natural pollutants present in the automotive exhaust, i.e., the aromatics Benzene and Toluene. The multiplicity of aromatics emitted in a typical exhaust plume, and the absorption caused thereby, makes compensation for the aromatics very difficult, and also limits the accuracy of the measurement.

It should be appreciated that many of these problems are compounded when the exhaust gas pollution detection system is required to be portable, and also to be capable of being operated in less than ideal surroundings, such as when it is desired to monitor vehicles that are traveling on a roadway, such as a highway or freeway.

SUMMARY OF THE INVENTION

In accordance with the present invention, a light source radiates an infrared beam that passes through a chopper, an exhaust plume of a motor vehicle passing in front of the source, a calibration cell and impinges on a multi-element photosensor. The photosensor unit includes a plurality of photodetectors which are spaced closely adjacent to each other and simultaneously sense the beam after it propagates through the plume. The placement of the chopper at the source improves the detection accuracy by removing the IR radiation emitted by the plume. The calibration cell provides for convenient and accurate calibration of the system.

The photodetectors are sensitive to different wavelengths corresponding to spectral absorption peaks of constituents of the composition of the plume, including carbon monoxide (CO), carbon dioxide ($CO_2$), hydrocarbon (HC), water vapor ($H_2O$) and nitric oxide (NO). A computer computes the composition of the plume as percentages of the constituents based on the sensed transmittances of the respective wavelengths through the plume.

An optical beam homogenizer disposed between the plume and the photosensor causes the light incident on the photodetectors to have uniform intensity and removes the spatial variation of the constituents. A video camera produces a video image of the vehicle license plate, and a frame grabber causes the video image to be displayed on a video monitor and recorded on a video recorder, magnetic disk or magneto-optical disk together with the plume composition data.

Although especially suitable for vehicle emission sensing, the present invention can also be utilized for sensing the composition of fluids (gases and liquids) in a variety of diagnostic and regulatory applications, such as industrial and waste-site chemical pollution monitoring.

The present invention overcomes the drawbacks of the prior art system discussed above. The photodetectors are spaced closely adjacent to each other in a single detector assembly which is cooled by a single cooling unit and uniformly illuminated by the light beam through the beam homogenizer after propagation through the vehicle exhaust plume.

The present system does not include a rotating filter wheel or similar moving parts, or a beam splitter or other components which require critical alignment. The invention is therefore inexpensive to manufacture on a commercial production basis, and suitable for mass deployment for regulatory and other purposes.

The photodetectors are integrally fabricated on a single substrate to enable isothermal operation and minimize their size and weight. This enables the characteristics of the photodetectors to be precisely matched under varying temperature and illumination conditions, with a substantial increase in measurement accuracy and reliability over the prior art. A preferred photodetector has reflector layers behind respective photosensitive elements. The reflector layers create a "double pass" through the photosensitive elements, which allows the elements to be optically thin while maintaining a high sensitivity. The "double pass" configuration reduces scattering in the substrate which minimizes optical cross-talk between the elements. This allows the detectors to be spaced closer together.

These and other features and advantages of the present invention will be apparent to those skilled in the art from the following detailed description, taken together with the accompanying drawings, in which like reference numerals refer to like parts.

BRIEF DESCRIPTION OF THE DRAWINGS

The above set forth and other features of the invention are made more apparent in the ensuing Detailed Description of the Invention when read in conjunction with the attached Drawings, wherein:

FIGS. 3 to 7 are simplified sectional views illustrating alternative embodiments of the photodetector assembly;

FIG. 18 is a graph illustrating the relationship between optical transmittance and gas composition for CO and $CO_2$ in accordance with the invention;

FIG. 19 is a graph illustrating the relationship between carbon dioxide concentration and carbon monoxide concentration as sensed by the apparatus.

DETAILED DESCRIPTION OF THE INVENTION

Figure 1:
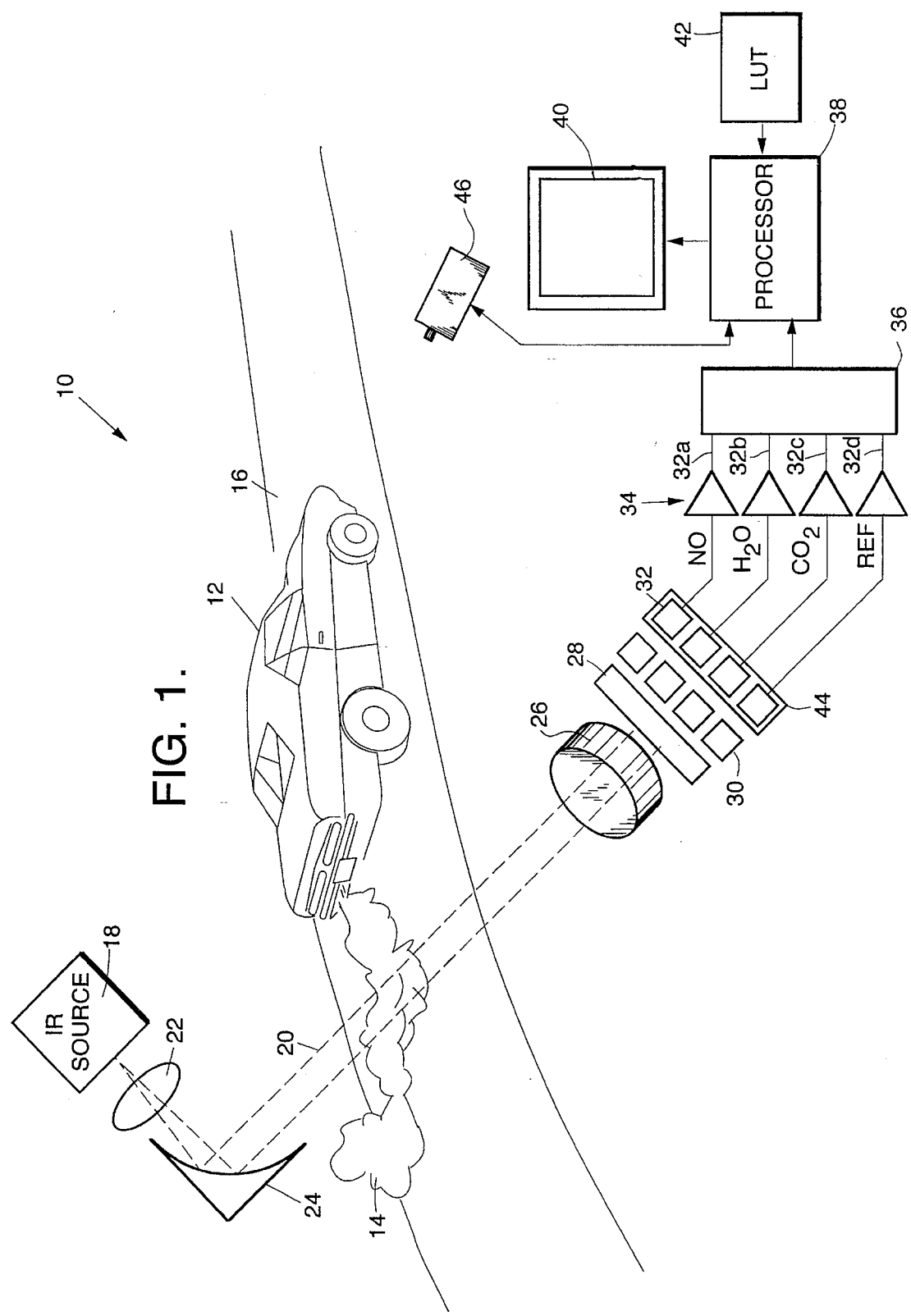
FIG. 1 is a simplified pictorial view of an optical sensing apparatus for remotely measuring the exhaust gas composition of moving motor vehicles in accordance with the present invention.

FIG. 1 is an overall system diagram that illustrates a multi-channel sensor system 10 for measuring the exhaust gas composition of a vehicle 12 that emits an exhaust plume 14 as the vehicle travels along a roadway 16. It should be understood that the vehicle 12 does not form a part of the system 10. It should be further understood that this invention can also be used to quantify emissions from a smokestack, a chimney, and the like, and is not limited for use only with vehicles having internal combustion engines that emit $CO_2$, CO, HC, $H_2O$ and NO as constituents of their exhaust gas. In general, this invention is applicable to the determination of the pollutant concentration in a gas plume emitted by any natural or man-made source.

The system 10 includes an IR source 18, preferably a broadband IR source such as a glow bar, that has a significant IR radiation output in the range of approximately 3 micrometers to approximately 6 micrometers. The IR source 18 provides a beam 20 that may optionally be passed through a chopper 22 (nominally 200 cycles per second) and a beam former 24, such as a parabolic reflector. The beam 20 is disposed so as to pass through the exhaust gas plume 14 of the vehicle 12 when the vehicle is in motion on the roadway 16. The passage of the IR beam 20 through the exhaust gas plume 14 results in the selective partial absorption of various wavelengths within the broadband beam, the selective absorption occurring because of the presence of NO, water vapor, $CO_2$, CO, HC and other molecular species within the exhaust gas.

After passing through the plume 14 the beam 20 passes through an optional IR-transparent gas cell 26 (FIG. 15), used for calibration purposes, and then through a beam integrator or diffuser 28. The diffused beam is applied to a plurality n of narrow band filters 30, where n is equal to a number of system 10 measurement channels. Each filter 30 is selected so as to pass a predetermined narrow band of wavelengths to an associated one of a plurality of IR detectors 32 in a detector assembly 31. Each detector 32 outputs an electrical signal to an input of a corresponding measurement channel comprised of suitable analog electronics 34 (e.g. amplifiers), an n channel analog to digital (A/D) converter 36, and a data processor 38 having an associated output device 40. The data processor 38 provides the required signal processing of the outputs from the A/D converter 36. The data processor 38 is coupled to a lookup table (LUT) 42, the use of which is described in detail below. The LUT 42 is most readily implemented as a region of memory (semiconductor and/or disk) that is accessible by the data processor 38. A suitable cooler 44, such as a thermo-electric (TE) device, is employed for cooling those types of IR detectors 32 which are required to be cooled to an operating point that is below ambient temperature.

In a presently preferred embodiment of this invention there are six spectral measurement channels. These are an NO spectral channel 32a (having a filter 30 with a passband centered on 5.26 µm), an $H_2O$ spectral channel 32b (having a filter 30 with a passband centered on 5.02 µm), a first reference, or $CO_2$ spectral channel 32c (having a filter 30 with a passband centered on 4.2 µm), a CO spectral channel 32d (having a filter 30 with a passband centered on 4.6 µm), a HC spectral channel 32e (having a filter 30 with a passband centered on 3.3 µm) and a second reference (REF) spectral channel 32f (having a filter 30 with a passband centered on 3.8 µm). Additional channels to measure other pollutants can also be added if desired.

In general, the NO spectral channel 32a is located near resonant absorption peaks in the vicinity of 5.2 µm; the water vapor spectral channel 32b is in a region of strong water absorption where fundamental lines do not saturate; the first reference spectral channel 32c is employed for normalizing the pollutants to the normal combustion products, i.e., $CO_2$; and the second reference (REF) spectral channel 32f is provided at a region in which no atmospheric or automotive emissions gases absorb.

The REF spectral channel compensates the other five spectral channels for variations caused by: (a) fluctuations in the output of the IR source 18 during the passage of the vehicle; (b) particulate matter in the form of road dust; (c) particulate matter in the exhaust gas plume 14; (d) infrared radiation emitted from the exhaust plume, and any other factors that may reduce the amount of illumination reaching the detectors 32. The REF spectral channel thus operates to provide a baseline output which is independent of the molecular species (NO, $H_2O$, $CO_2$, CO and HC) being measured. The output of the REF spectral channel 32f is used to normalize, such as by dividing, the five molecular species spectral channels 32a–32e.

Figures 2, 11:
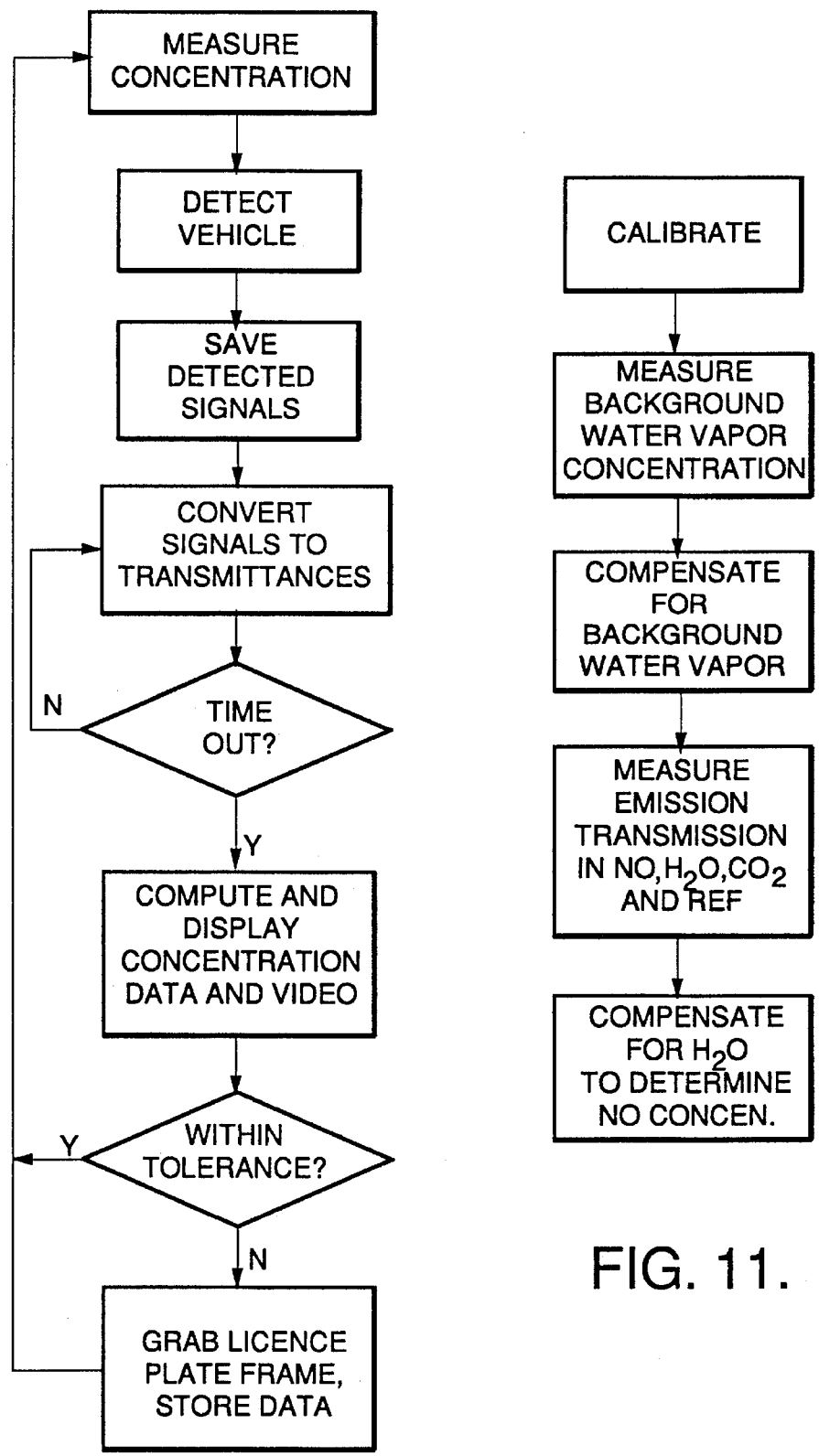
FIG. 2 is a logic flow diagram that illustrates a method of this invention for monitoring the exhaust emissions of vehicles traveling on a roadway.
FIG. 11 is a logic flow diagram that illustrates a method of this invention for determining the NO concentration in an exhaust plume.

The overall operation of the system 10 is illustrated in the flowchart of FIG. 2. The system 10 is suitable for attended operation or for unattended operation, once the components have been set up and calibrated. The system 10 periodically measures the constituent concentrations of the air at the rate of the chopper. When a vehicle 12 passes through the beam 20, the amplitudes of the output signals drop sharply and then rise. This triggers the A/D 36 and data processor 38 to save the output signals measured in the clean air immediately preceding the vehicle and to save the output signals taken in the vehicle exhaust plume 14 immediately following the vehicle for a predetermined period.

The use of a chopper positioned at the detectors is well known in the art for removing the detectors' quiescent levels. In such a configuration the data processor 38 measures the output signals when the photodetectors 32 are blocked and unblocked by the chopper 22, and calculates the peak-to-peak difference signals over the predetermined period, thereby subtracting out the photodetectors' quiescent output levels. A normalized transmission level for each constituent of the plume would be computed by forming a ratio of the peak-to-peak signals measured through the plume and in the clean air in front of the vehicle and normalizing it by a similar ratio for the reference signals. In this configuration the constituent measurements are distorted by irradiance from the plume itself.

In the preferred embodiment positioning the chopper at the IR source enables the system to distinguish infrared radiation emitted by the source from that emitted by the vehicle exhaust. When the chopper blocks the beam, the detectors measure the infrared radiation emitted from the plume. The data processor calculates the peak-to-peak signal which removes the quiescent levels of the detectors as well as the interference from the vehicle exhaust. Thus, the measurements of the transmission levels are more accurate.

The data processor 38 then computes the composition of the plume 14 in terms of the percentage or concentrations of the constituents NO, $CO_2$, CO and HC based on the amplitudes of the signals from the photodetectors 32. This data may be displayed, together with the video from the camera 46, on the monitor 40 as illustrated in FIG. 1. This computation is performed rapidly, for example one-half second, which is sufficient for the system 10 to produce an accurate measurement and reset for the next vehicle. The data processor 38 then determines if the composition is within specified regulatory tolerances. If so, the apparatus 10 resets and collects data until the next vehicle passes. If not, indicating that the vehicle 12 is producing excessive pollution, the data processor 38 inputs a frame of video from the camera 46, the video including an identifying characteristic of the vehicle 12, such as an image of the license plate, superimposes the concentration data on the video frame, and stores the combined video and data frame in a mass storage device such as a hard drive.

The data can be retrieved at a later time for enforcement use, such as sending a notice of violation to the owner of the vehicle. It is also within the scope of the invention to store a combined video and data frame for every vehicle which passes through the beam 20, rather then just polluting vehicles, for applications such as generating a database of exhaust gas composition for different types and makes of vehicles.

Figure 3:
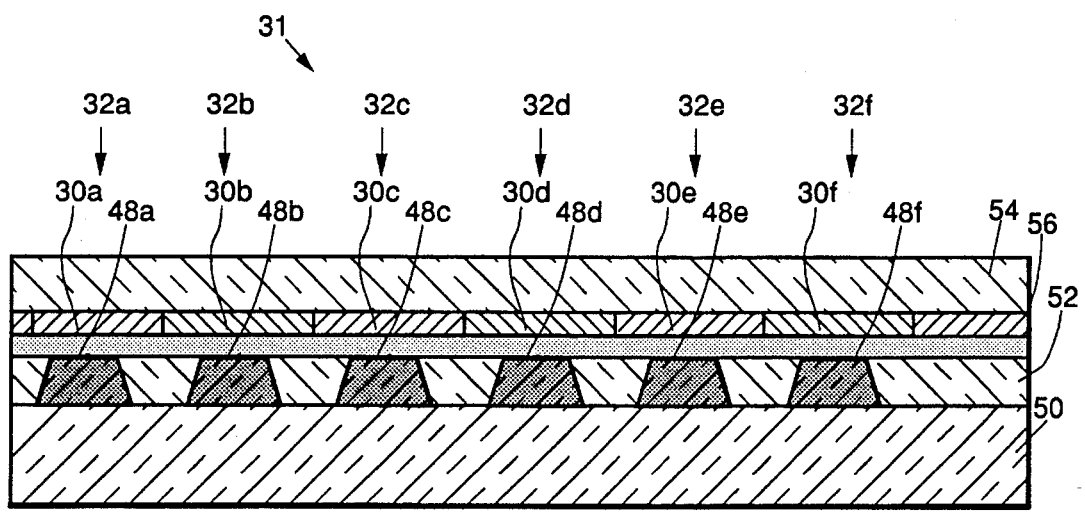

The photodetector assembly 31 is illustrated in FIG. 3. The photodetectors 32a–32f include photosensitive elements 48a–48f which are integrally fabricated on a substrate 50. The elements 48a–48f are preferably photoconductive and formed of mercury cadmium telluride (HgCdTe or HCT), whereas the substrate 50 is cadmium zinc telluride (CdZnTe).

However, the invention is not so limited, and the photodetectors 32a–32f can be fabricated using other group II-VI material systems such as mercury zinc telluride (HgZnTe), lead salts or group III-V materials. The photosensitive elements 48a–48f can also be photovoltaic rather than photoconductive.

The photosensitive elements are optically isolated from each other by an opaque material 52 such as alumina to minimize optical cross-talk. Optical filters 30a through 30f having passbands centered on 5.26, 5.02, 4.2, 4.6, 3.3, and 3.8 micrometers respectively are formed on a transparent substrate 54 and adhered to the elements 48a–48f respectively by an optically transparent adhesive 56. The substrate 50 is typically formed of germanium (Ge), whereas the filters 30a–30f are formed as dielectric stacks including multiple layers of zinc sulfide (ZnS).

The elements 48a–48f are approximately 1×1 millimeter in size, although the invention is not so limited, which is large enough to accommodate the filters 30a–30f, but small enough to achieve a high signal-to-noise ratio. The integral design of the photodetector assembly 31 ensures that the photodetectors 32a–32f operate isothermally, thereby eliminating inaccuracies resulting from temperature differences. The assembly 31 is regulated to a temperature of approximately 200° K. by the cooler 44.

Figure 4:
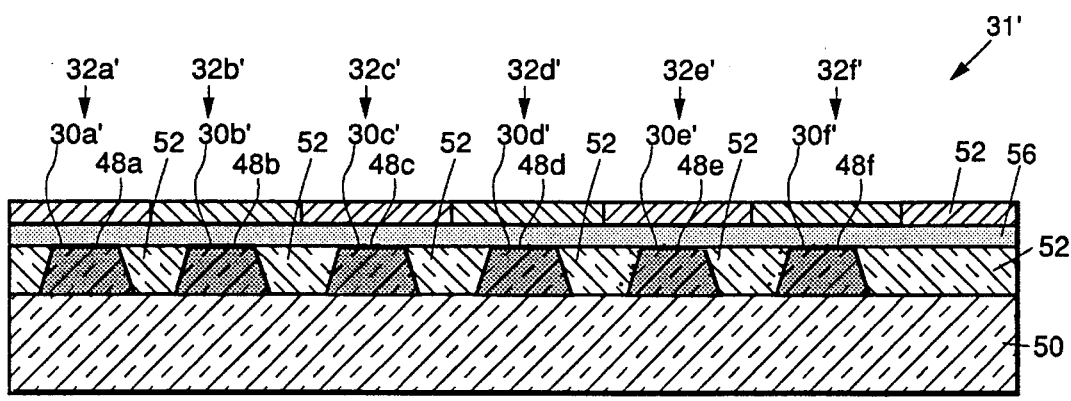
Figure 5:
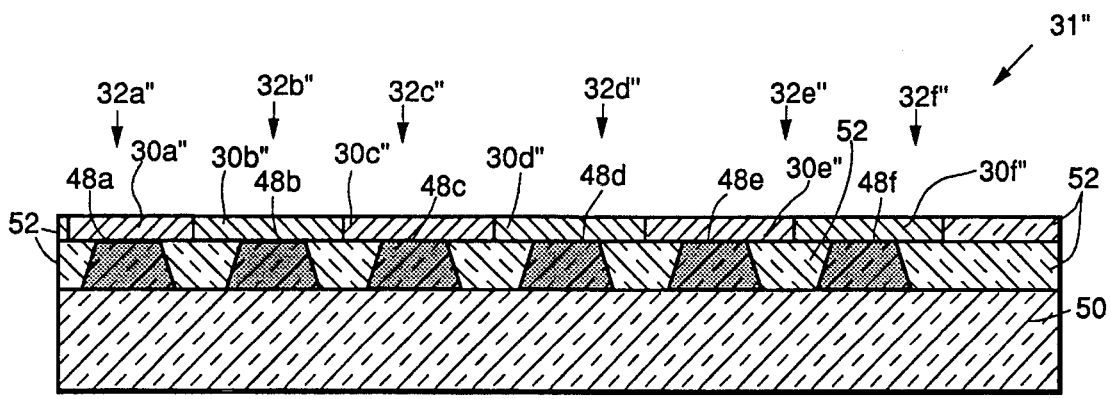

FIG. 4 illustrates a modified photodetector assembly 31', in which like elements are designated by the same reference numerals used in FIG. 5, and corresponding but modified elements are designated by the reference numerals primed. The assembly 31' differs from the assembly 31 in that the substrate 54 is removed after filters 30a'–30f' have been adhered to the elements 48a–48f and opaque material 52 by the adhesive 56.

FIG. 5 illustrates another modified photodetector assembly 31' in which like elements are designated by the same reference numerals used in FIG. 5, and corresponding but modified elements are designated by the same reference numerals double primed. The assembly 31" differs from the assembly 41 in that the substrate 54 and adhesive 56 are omitted, and filters 30a"–30f" are formed directly on the photosensitive elements 48a–48f respectively.

FIG. 6 illustrates an alternative photodetector arrangement for practicing the invention, with the filters not shown for simplicity of description. The individual photodetectors are interchangeable, and will be described collectively.

A photodetector assembly 58 includes a substrate 60. Reflector layers 62 of a suitable material such as gold are formed on the substrate 60. Photosensitive elements 64 of HCT or other suitable materials which are highly sensitive to the wavelengths they are intended to detect are adhered to the reflector layers 62 by optically transparent adhesive 66. The lateral areas between the elements 64 and reflector layers 62 are filled with opaque material 68.

Light incident on the photosensitive elements 64, after passing through the plume 14, passes through the elements 64 and is reflected back into the elements 64 by the respective reflector layers 62. This "double pass" minimizes optical cross-talk between the elements 64 by reducing scattering in the substrate 60. The "double pass" increases the light detecting efficiency of the detector which allows the photosensitive elements 64 to be thinner by approximately half, typically about 1 micron, than they would be in a conventional single pass detector. The "thinness" of the elements reduces the optical cross-talk between the elements by further reducing scattering of the incident radiation while still achieving good quantum efficiencies of greater than approximately 60%.

FIG. 7 illustrates another alternative photodetector assembly 68 for practicing the invention, including a substrate 70 of optically sensitive material such as CdZnTe. Photosensitive elements 72 of HCT or other suitable material are formed on the substrate 70. The lateral spaces between the elements 72 are filled with an opaque material 74. An anti-reflection coating 76 is formed on the back side of the substrate 70, and an absorbing layer 78 having high optical absorption efficiency is formed on the coating 76. The coating 76 and layer 78 are typically formed of $ZnS_2$.

Light from the beam 20 which is incident on the photosensitive elements 72 passes through the elements 72, substrate 70 and coating 76 and is absorbed by the absorbing layer 78. The coating 76 prevents light from being reflected from the layer 78 back to the elements 72. This arrangement also enables efficient photodetection with low optical cross-talk.

Figure 8:
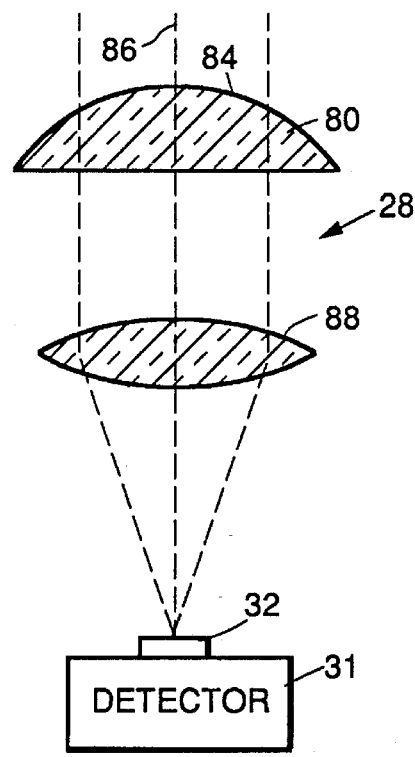
FIG. 8 is a simplified elevational view illustrating the photodetector assembly in combination with a beam homogenizer.
Figure 9:
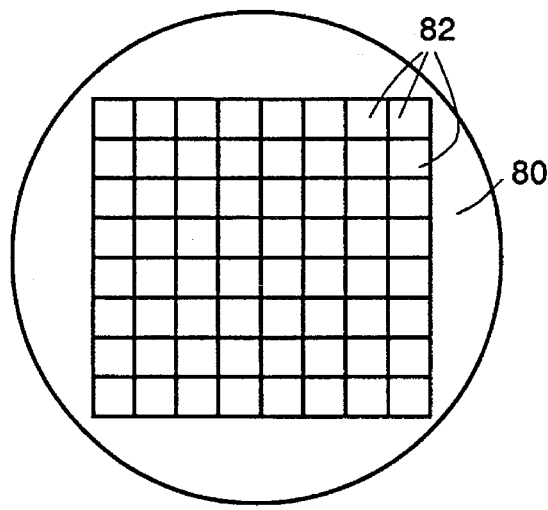
FIG. 9 is a plan view of the beam homogenizer.
Figure 10:
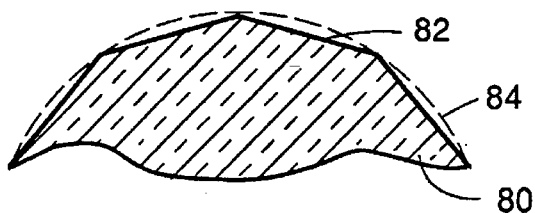
FIG. 10 is a fragmentary sectional view of the beam homogenizer illustrated at enlarged scale.

The beam integrator 28, which is illustrated in FIGS. 8, 9 and 10, homogenizes the beam 20 after propagation through the plume 14 to remove the spatial and temporal variations of the constituent concentrations so that the detected signals are synchronized. The optical intensity or energy that is incident on the photodetectors is substantially uniform throughout the cross-section of the homogenized beam 20. This ensures that the same homogenized or averaged scene is sensed by the photodetectors 32, and substantially increases the accuracy of the measurement by reducing the spatial and temporal variance of the constituent concentrations by over an order of a magnitude. The integrator enables synchronous operation of the photodetectors.

The beam integrator 28 preferably includes a planoconvex lens 80. A rectangular array of flat facets 82 are formed in a convex surface 84 of the lens 80. The facets 82 refract segments of light from respective portions of the incident beam 20 toward a central axis 86 such that the refracted light segments are superimposed with each other to form a series of overlapping rectangles on the photodetectors 32. The superimposed image which is incident on the detectors 32 is a homogenized or averaged rectangular image segments refracted from the facets 82, and thereby represents the average intensity of the beam 20. A converging lens 88 may optionally be employed for reducing the size of the homogenized image on the photodetectors 32.

The principles of a preferred embodiment of the beam integrator 28 are disclosed in U.S. Pat. No. 4,195,913, entitled "OPTICAL INTEGRATION WITH SCREW SUPPORTS", issued Apr. 1, 1980 to D. Dourte. A beam integrator that is suitable for practicing the invention is commercially available from Spawr Optical Research, Inc. of Corona, Calif.

It should be realized that the configuration of the beam integrator 28 suitable for practicing the invention is not limited to the multifaceted embodiment design illustrated in FIGS. 8 to 10. For example, the beam integrator 28 can also be embodied using a reflective, rather than a refractive implementation as disclosed by Dourte.

A method of this invention for measuring the NO component of the plume, illustrated in FIG. 11, includes the following steps: (A) calibration of the system 10 using the cell 26; (B) measurement of the background water vapor concentration utilizing the water band absorption (for example, at wavelengths such as 1998 cm$^{-1}$ or 2023 cm$^{-1}$); (C) background normalization for water vapor absorption in the NO band; and (D) real time measurements of automotive exhaust transmission in the NO, water vapor, and $CO_2$ spectral channels 32a–32c, augmented by a next step (E) of algorithmically compensating for the water emitted by the vehicle 12 through the use of the lookup table 42. As was described above, the lookup table 42 contains entries which relate absorption by water vapor in the water spectral channel 32b to absorption by water vapor in the selected NO spectral band(s).

Figure 12:
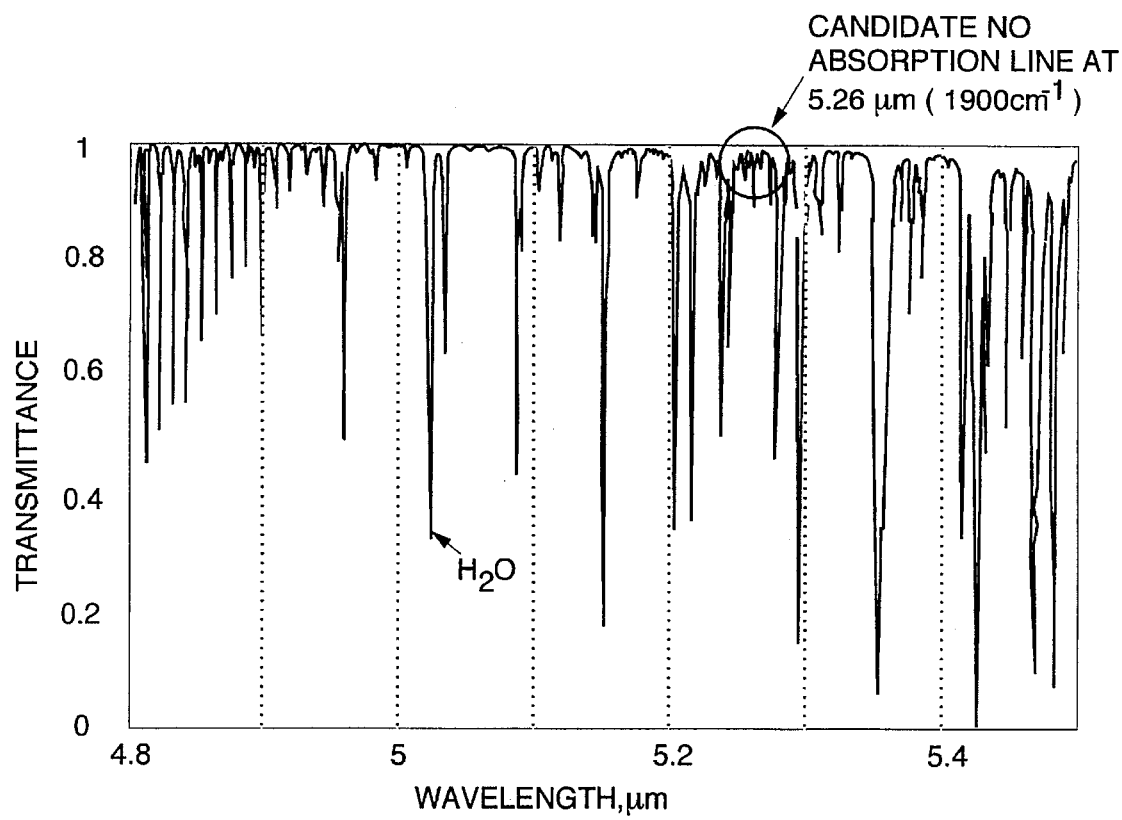
FIG. 12 graphically illustrates the close proximity of the water vapor absorption spectrum to the desired NO absorption spectrum.

In this regard FIG. 12 shows a spectral region of interest around 5.26 μm, one of the preferred NO absorption lines. The water absorption band is shown at approximately 5.02μm. The REF region at approximately 3.8 μm is not shown.

Figure 13:
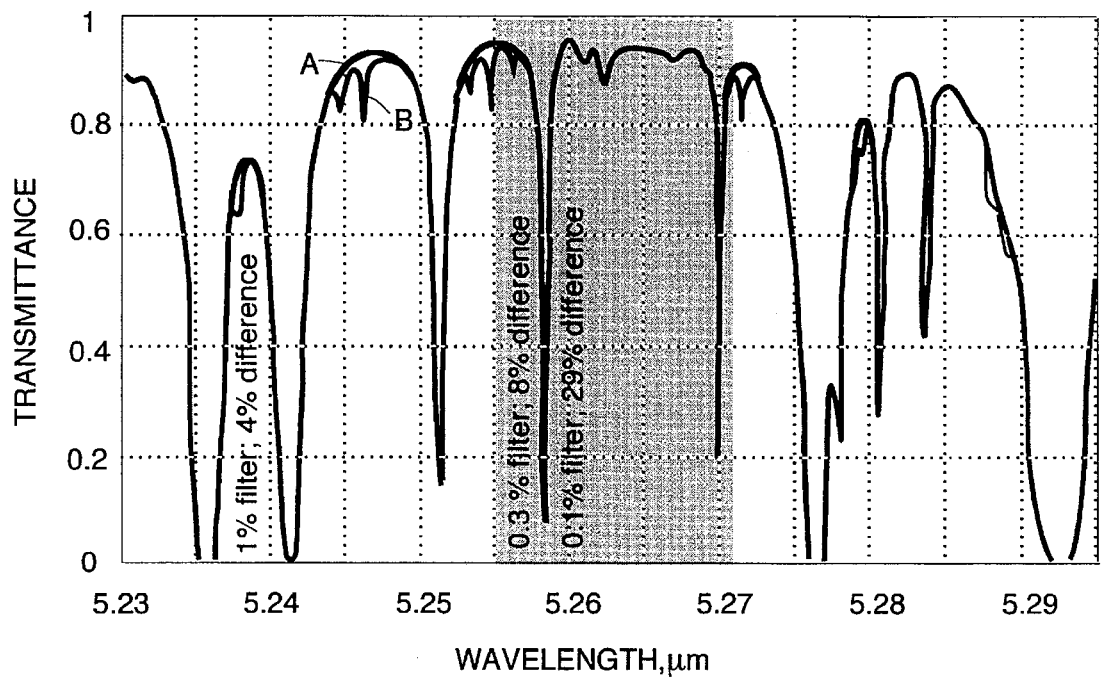
FIG. 13 graphically illustrates the effect of different ideal filters on the measurement of the NO absorption band.

FIG. 13 shows an expanded spectrum around the 5.26 μm NO line and illustrates the use of several different spectral widths (0.1%, 0.3%, and 1%) for the NO filter 30. The heavy line (designated "A") illustrates a 60% relative humidity case with zero ppm NO in the exhaust plume 14, while the lighter line (designated "B") illustrates the 60% relative humidity case with 1000 ppm NO in the exhaust plume 14. The graph of FIG. 13 assumes "perfect" passband filters 30 having vertical sides and 100% transmittance. The "percent difference" term is a measure of the effect of the NO on the area under the curve.

A fraction of NO absorption to water absorption is shown in Table 1 as a function of relative humidity and spectral passband (as determined by the particular one of the filters 30 that is utilized).

TABLE 1

Ratio of Absorption by 1000 ppm NO to Absorption by Water in a Spectral Band Around 5.2 μm as a Function of Spectral Filter Width and Relative Humidity

| Filter Width | RELATIVE HUMIDITY AT 90° F. | | | |
|---|---|---|---|---|
| | 0% | 30% | 60% | 90% |
| 0.1% | 184% | 54% | 29% | 18% |
| 0.3% | 13% | 12% | 8% | 5% |
| 1.0% | 15% | 5% | 4% | 3% |

The entries of Table 1 also take into account the presence of water vapor that is present in the exhaust gas plume 14. As shown, and for a 60% relative humidity across, by example, a 30 foot optical path length and a 1000 ppm NO concentration, the ratio of relative absorption of the water line to the relative absorption due to the NO varies from 29% for a 0.1% filter to 4% for a 1% filter. This ratio thus determines the accuracy of the field/laboratory calibration necessary to measure NO at a given sensitivity. For example, in the case of a 1% filter the ratio of integrated NO absorption to spectral water absorption is 4%. Hence with a 2% accuracy in the lookup table correction, 500 ppm of NO is the limit of detection at 60% R.H and a 30 foot spacing between the IR source 18 and the detectors 32. In contrast, with an NO filter 30 having a 0.1% passband the concentration ratio is 29%. For this case with a 2% accuracy in the lookup table correction 100 ppm of NO is the limit of detection at 60% R.H. and a 30 foot spacing.

The following is an example of the $NO_x$ lookup table 42.

| % | Absorption $C_{H2O}$ (Band 1) | Transfer Function $T = C_{H2O}$ (Band 1) / $C_{H2O}$ (Band 2) | Absorption $C_{H2O}$ (Band 1) |
|---|---|---|---|
| 1.0 | .0011014 | 3.205 | .00353012 |
| 2.0 | .00210755 | 3.205 | .00673933 |
| 3.0 | .0030484 | 3.205 | .00977024 |

Figure 14:
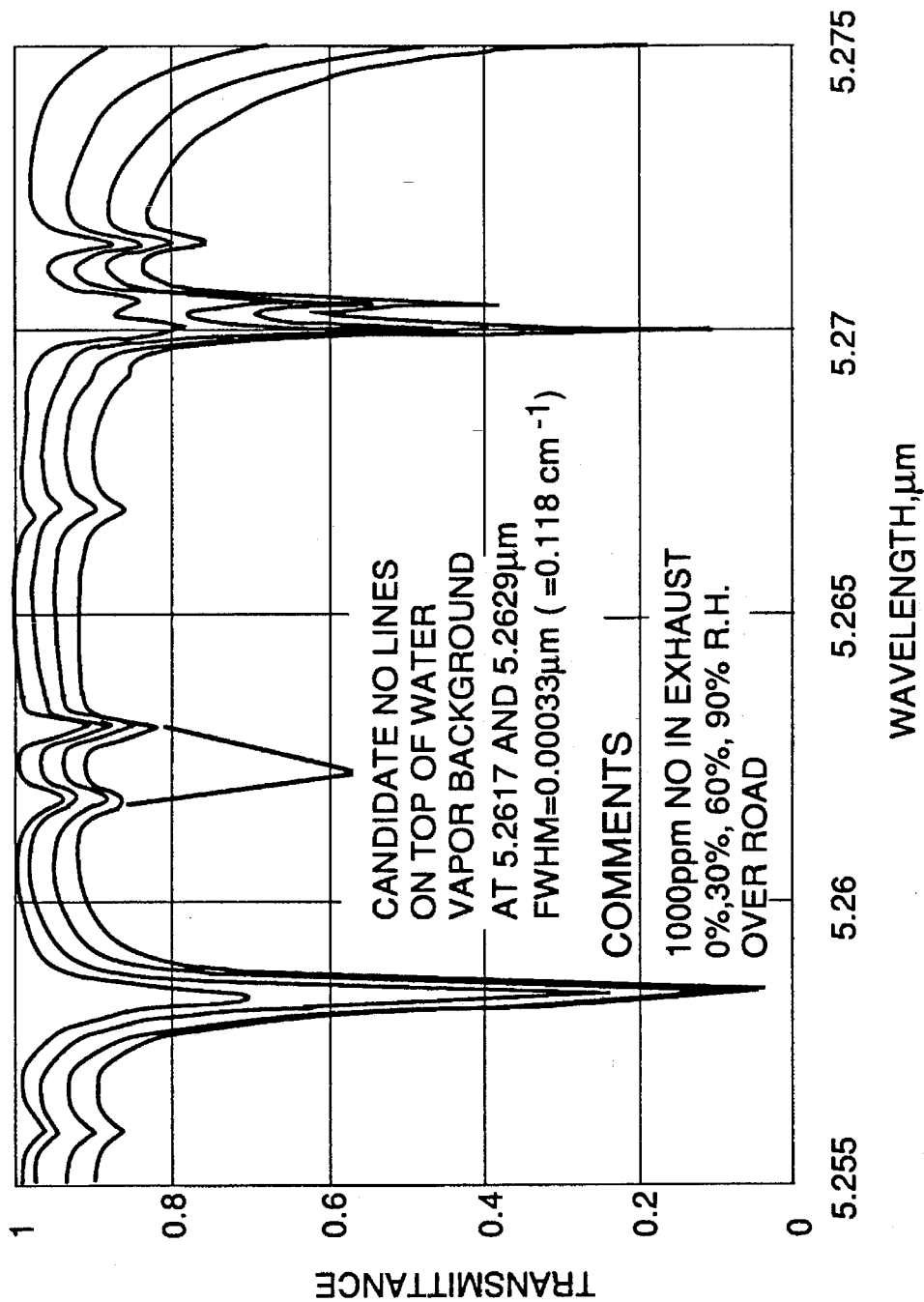
FIG. 14 graphically illustrates two candidate NO spectral lines (5.2617 µm and 5.2629 µm) atop background water vapor lines for different relative humidity levels, and makes evident a requirement to subtract the water vapor background.

The graph of FIG. 14 illustrates the importance of subtracting out or compensating for the absorption due to the water vapor background. In FIG. 14 the spectral plots for different amounts of relative humidity illustrate the monotonic offset in the NO baseline vs relative humidity. This linear shift, corresponding to a flat top absorption integral, is compensated for very accurately if a narrow band NO filter 30 is utilized.

Figure 15:
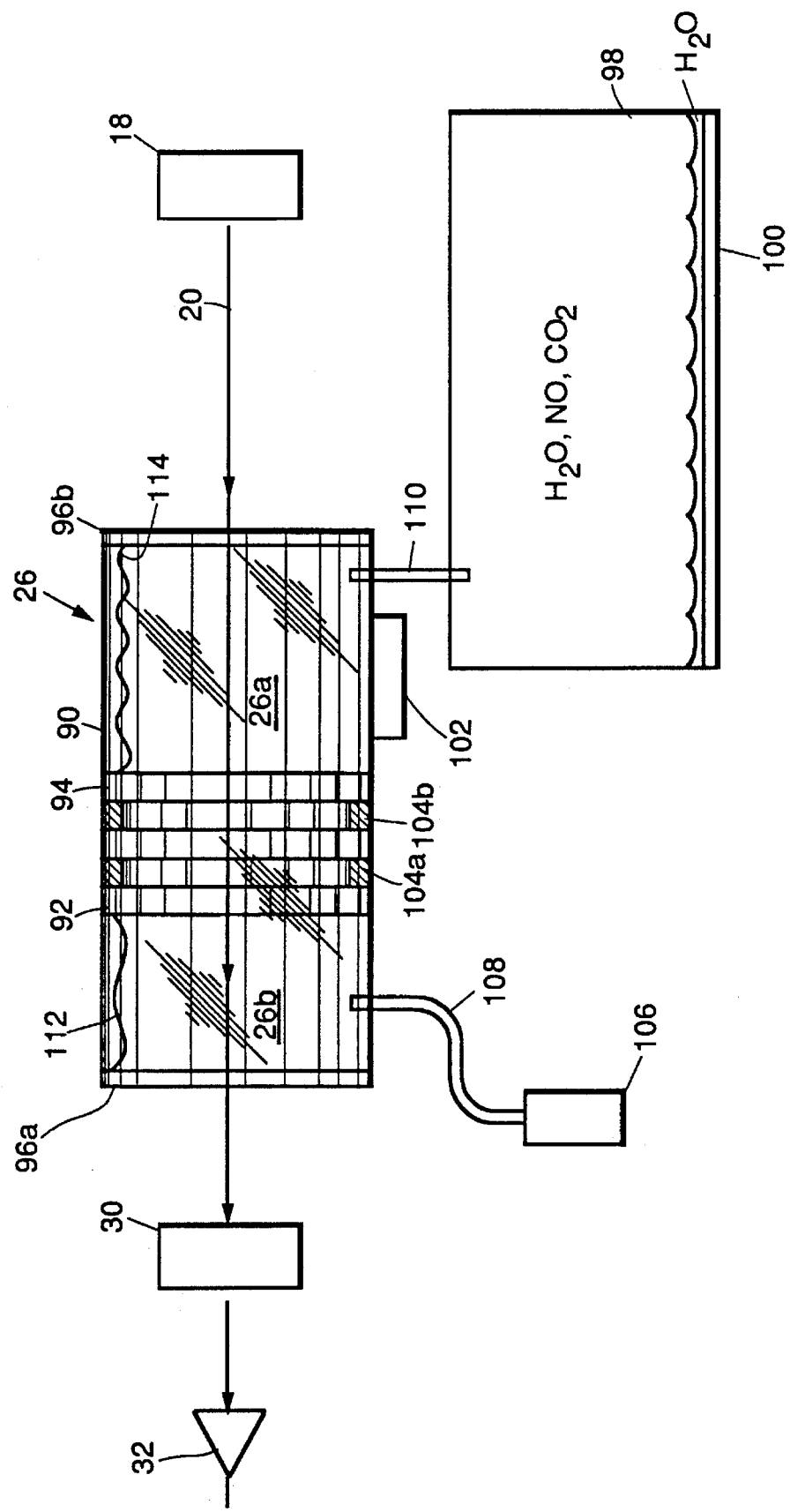
FIG. 15 is a simplified cross-sectional view (not to scale) of a gas calibration cell in accordance with an aspect of this invention.

Calibration with respect to variations in the illumination provided by the source 18 across the various detectors 32 is preferably accomplished using the heated calibration cell 26 that is depicted in FIG. 15.

In accordance with an aspect of this invention the calibration cell 26 is comprised of a housing 90 that is divided into two compartments 26a and 26b by a pair of IR-transparent pistons 92 and 94. The housing 90 has IR-transparent windows 96a and 96b at opposing ends thereof for permitting passage of the beam 20 through the housing, and also through the transparent pistons 92 and 94. The compartment 26b contains a heated mixture of gases of interest (e.g., NO, $CO_2$, $H_2O$, CO and HC) in a desired percentage. The calibration gas mixture is maintained at a temperature of, by example, approximately 100 C. The concentration path length product within the sealed cell 26 is varied by redistributing the mixture of gases between the optically transparent compartment 26b and an attached leak tight gas reservoir 98, which may also contain a liquid water source. The reservoir 98 includes a heater 100, and the compartment 26a also includes a heater 102 for maintaining the desired temperature.

Mechanical variation of the path length through the cell 26 is accomplished by magnetically driving the piston 94 with the piston 92 through two annular permanent or electrically activated magnets (104a and 104b). This is accomplished with a pressurized gas (air) tank 106 and a conduit 108 which is connected to the chamber 26a. Pressurizing the compartment 26a causes the piston 92 to move to the right in the drawing, thereby exerting a repelling magnetic force on the piston 94 through the magnets 104a and 104b, This causes the piston 94 to also move to the right, thereby reducing the volume of the gas mixture in the chamber 26a through conduit 110 and sealed reservoir 98, and thus varying the path length product within the cell 26. A restoring force is applied by compression springs 112 and 114.

The use of the calibration cell 26 enables the NO, $H_2O$ $CO_2$, CO and HC detectors 32 to be rapidly calibrated in the field with respect to each other. Significantly, in that the cell 26 is a sealed system no gases are released to the atmosphere and, as a result, it is not necessary to purchase and transport replacement calibration gas canisters. In that NO is considered to be a toxic substance, this is a significant advantage.

During the actual measurement of one or more exhaust plumes the calibration cell 26 can be removed from the beam. Alternately, the calibration cell 26 can be controlled to reduce the volume of the chamber 26a to zero. The minimal absorption of the beam 20 as it passes through the cell 26 is compensated by the REF spectral channel measurement, as was previously described. The use of other approaches, such as a bellows or rotary to linear feedthroughs, are also within the scope of this invention.

In the operation of the system 10 a signal processing routine executed by the data processor 38 of FIG. 1 carries out the method depicted in FIG. 11. The data processor normalizes the signal in the NO band by both the transmission determined in the REF channel and the transmission determined in the water vapor channel, converted by the use of the look up table 42 to a residual transmission of water in the NO band. This normalization is performed continuously both for background measurements and for dynamic emission measurements using the functional expression:

$T(NO)_{eff} = T(NO)/(T(H_2O) \times \{Lookup(H_2O \text{ band to NO band})\} \times T(REF))$, where $T(NO)_{eff}$ is the effective NO transmission, T(NO) is the measured NO transmission, $T(H_2O)$ is the measured water transmission, Lookup($H_2O$ band to NO band) is a predetermined water/NO absorption correction obtained from the lookup table 42, and T(REF) is the measured REF spectral channel transmission.

The relative NO concentration (% NO) in the exhaust plume 14 is derived from the foregoing expression using the transmission versus concentration of the NO detector 32 established during factory calibration and as updated during the field calibration utilizing the cell 26. The actual NO concentration in the exhaust gas plume 14 is determined as the ratio of NO in the plume 14 to the measured concentration of the $CO_2$ in the plume, multiplied by the relative concentration of $CO_2$ in the exhaust as determined using an effective C:H ratio for an "average" fuel. For example, a $CO_2$ concentration of 15% is a reasonable value for an exhaust plume that results from the combustion of an "average" fuel.

In other words, the method first determines the effective NO transmission from the measured NO transmission scaled by the (a) measured water transmission, (b) the lookup table factor, and (c) the REF channel output which compensates for particulates, dust and the like that may obscure the beam 20. Having determined the effective NO transmission, this value is converted to a relative NO concentration using the results obtained from factory calibrations, as last updated by the use of the known NO concentration within the calibration cell 26. Having determined the relative NO concentration, this value is converted to an actual NO concentration by using the measured $CO_2$ concentration, and assuming the effective C:H ratio for a typical fuel.

Figure 16A:
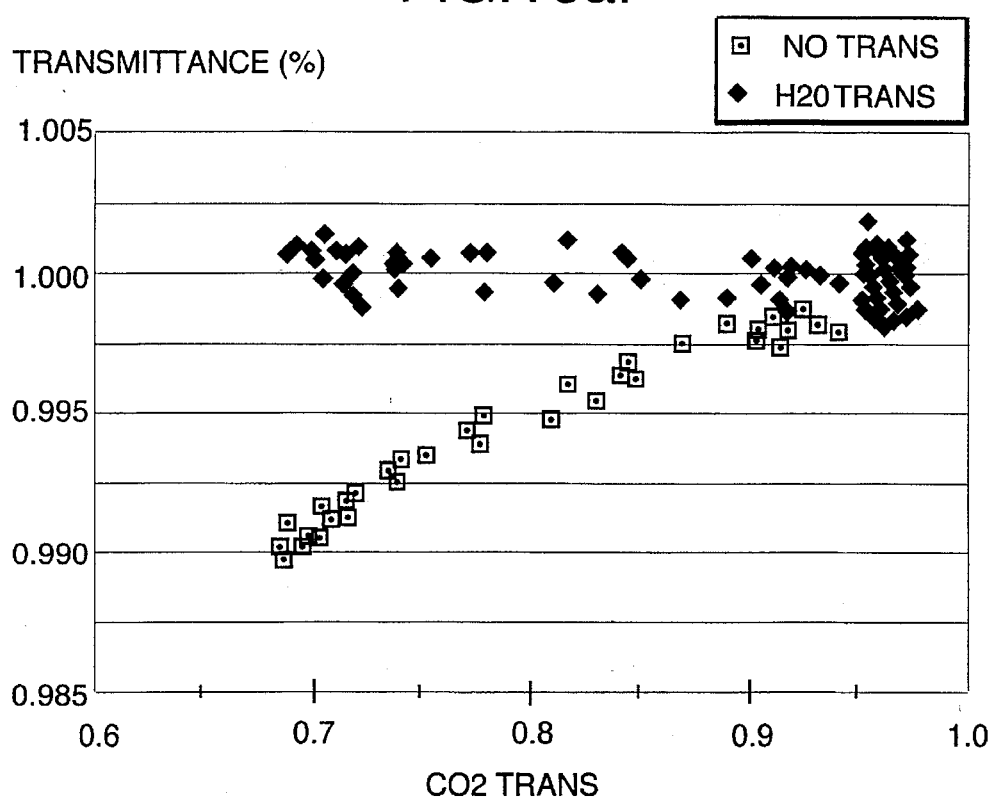
FIGS. 16a and b and FIGS. 17a, b and c are graphs illustrating the use of this invention in measuring NO emission from a high-emitting vehicle (1875 ppm) and a relatively low emitting vehicle, respectively, with FIG. 17a further showing the compensation for water vapor in the exhaust plume.
Figure 16B:
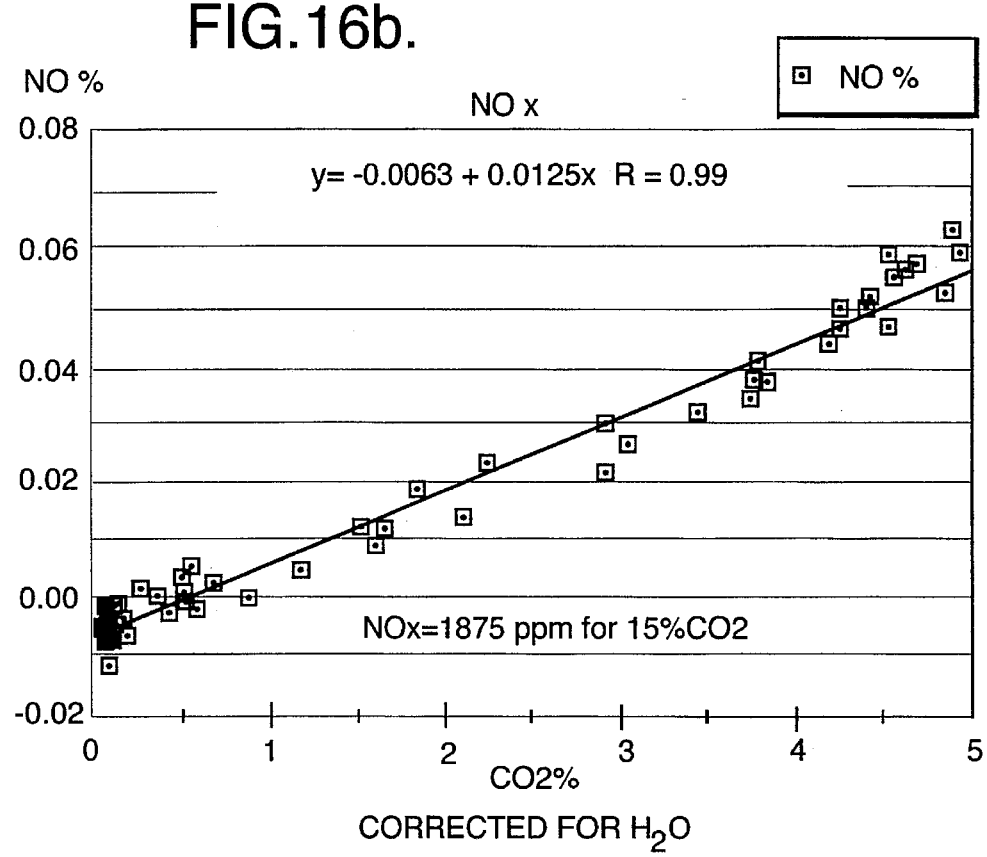

FIGS. 16a and b and FIGS. 17a, b and c are graphs illustrating the use of this invention in measuring an emission from a high-emitting vehicle (1875 ppm) and a relatively low emitting vehicle, respectively, with FIG. 17a further showing the compensation for water vapor in the exhaust plume.

The concentrations of $CO_2$, CO and HC as functions of the transmittances of the respective wavelengths of light as sensed by the photodetectors 32 are computed in a manner similar to that disclosed in the above referenced article to Bishop. The transmittance varies with constituent concentration in a non-linear manner as illustrated in FIG. 18.

The illustrated curves for $CO_2$ and CO were obtained experimentally over an absorption pathlength of 203 millimeters, and can be used as reference for computation and field calibration of the apparatus 10. A similar curve (not shown) exists for HC.

The $CO_2$ and CO constituents in the plume 14 disperse at the same rate. For this reason, the ratio of CO vs $CO_2$ is independent of the actual concentrations and the pathlength which vary over time, and can be measure directly. This ratio is in itself a useful indicator of the pollutant composition of the exhaust plume 14. A similar ratio is obtained for HC vs $CO_2$.

Since the plum progressively decays after emission from the tailpipe of the vehicle 12, the concentrations of the constituents $CO_2$ and CO will vary with time. However, their ratio will remain substantially constant. As shown in FIG. 19 the CO vs $CO_2$ ration can be expressed as the slope of a line 130 which can be computed by, for example, linear regression analysis of the individual data samples obtained over the sampling interval.

The parameters which are sensed directly by the apparatus 10 are concentration-pathlength products of the constituents. The pathlengths vary with time and are indeterminate. For this reason, the actual concentrations of the constituents cannot be measured directly.

However, the composition of the plume 14 in terms of percentage constituent concentrations is often required for regulatory purposes. This can be calculated with sufficient accuracy for practical use using the stoichiometric chemical relationships of the combustion process. A preferred example of such a computation for practicing the present invention is as follows.

The constituent concentrations in a nominal absorption pathlength of 10 centimeters is calculated using curves such as illustrated in FIG. 18. Calibration is performed periodically by placing the cell 26 in the path of the beam 20, and measuring transmittances $T_{CO}$, $T_{HC}$ and $T_{CO2}$ as a function of time during the dispersion of the gas. The concentration-pathlength product for the CO contained in the gas is determined from the measured transmittance $T_{CO}$. For each measurement of the concentration-pathlength product for CO, the concentration-pathlength product for HC and $CO_2$ is determined based on the measured concentration-pathlength product of CO and the known ratios of HC/CO and $CO_2$/CO in the calibration cell 26.

From the measured transmittances $T_{HC}$ and $T_{CO2}$, and the concentration-pathlength products determined for HC and $CO_2$, the relationships between transmittance and pathlength-products (such as those shown in FIG. 18), can be quickly determined for HC and $CO_2$. This is particularly important for $CO_2$ because it is a component in ambient air, hence, the relationship between concentration-pathlength product and transmittance will vary as a function of the distance between the light source 18 and the photosensor assembly 31.

For measurements of $CO/CO_2$ and $HC/CO_2$ in the exhaust plume of a moving vehicle, the transmittance $T_{CO}$, THC and $T_{CO2}$ are measured directly and concentration-pathlength products for CO, $CO_2$ and HC are determined from the relationships shown in FIG. 18 that result from the calibrations described above. Absolute tailpipe concentrations of CO, HC and $CO_2$ are then calculated using the following formulas.

% $CO_2$=42/(2.79 +2$T_{CO}$–0.37$T_{HC}$)

% CO=% $CO_2 \times T_{CO}$

% HC=% $CO_2 \times T_{HC}$

Derivation of % $CO_2$ is based on stoichiometric chemical balance in the combustion process using a "nominal fuel" having a carbon vs hydrogen ratio of 1.8.

For normal operation, the concentrations % NO, % CO, % $CO_2$ and % HC are displayed on the monitor 40 together with the video image of the license plate of the vehicle 12 as illustrated in FIG. 1 and stored as frames by the video recorder 46.

Figure 20:
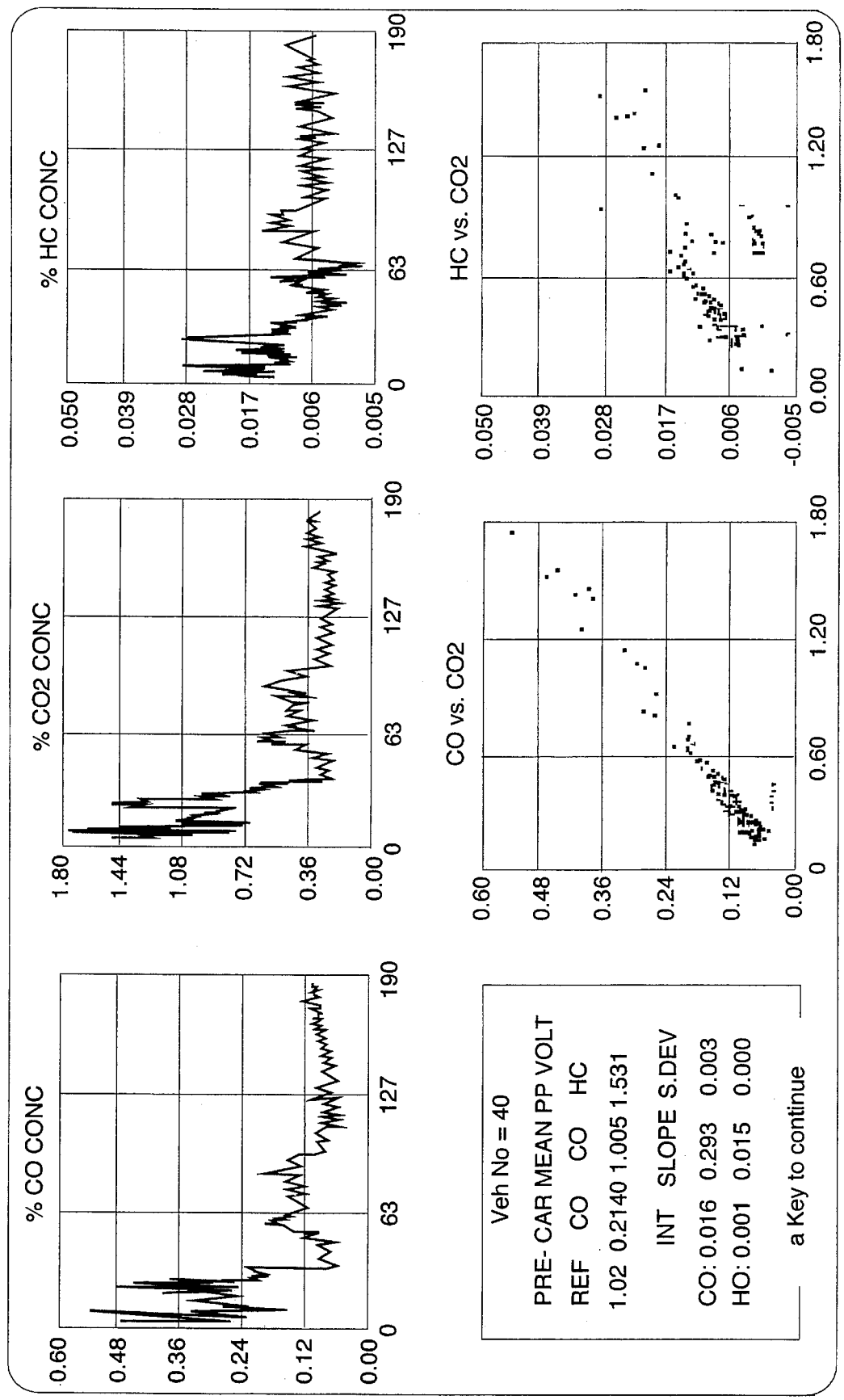
FIG. 20 is a diagram illustrating a data display of the apparatus.

FIG. 20 illustrates an expanded data screen which can be displayed on the monitor 40 if more information is required. The display of FIG. 20 includes the concentrations % CO, % $CO_2$ and % HC as a function of time (with 200 equivalent to one second at a sampling rate of 200 samples/second) and the peak-to-peak voltage outputs of the photodetectors 32, and the slopes, intercepts and standard deviations of the calculated CO vs $CO_2$ and HC vs $CO_2$ ratios.

A number of modifications can be made to the system 10 which will fall within the scope of this invention. As an example, the calibration cell 26 may not be required if the initial laboratory calibration of the detectors is considered to be sufficient. Also, other detectors can also be employed, with suitable filters, to measure other molecular species of interest.

Thus, while the invention has been particularly shown and described with respect to a preferred embodiment thereof, it will be understood by those skilled in the art that changes in form and details may be made therein without departing from the scope and spirit of the invention.

We claim:

1. A sensing apparatus for sensing a composition of an exhaust plume of a motor vehicle, comprising:

a light source for radiating light including a plurality of predetermined wavelengths through said plume;

a chopper positioned between said source and said plume for alternating blocking and passing said light;

a photosensor for simultaneously sensing alternating blocked or passed radiation levels at said predetermined wavelengths for said light passing through said plume; and a computer for computing transmittances of said predetermined wavelengths from respective differences between said blocked and passed radiation levels, and computing said composition as a predetermined function of said transmittances.

2. An apparatus as in claim 1, in which:

the photosensor comprises a plurality of photodetectors, each photodetector being sensitive to a band of wavelengths that includes only one of said predetermined wavelengths; and the photosensor is disposed such that said light from the light source is simultaneously incident on the photodetectors.

3. An apparatus as in claim 2, in which the photosensor further comprises light blocking members for optically isolating the photodetectors from each other.

4. An apparatus as in claim 2, in which the photosensor further comprises a substrate on which the photodetectors are substantially isothermally disposed.

5. An apparatus as in claim 4, in which the photosensor further comprises a temperature regulator for maintaining the substrate and photodetectors at a predetermined temperature.

6. An apparatus as in claim 2, in which each photodetector comprises:

a photosensitive element; and a filter disposed between said plume and the photosensitive element having a passband coinciding with said respective band of wavelengths.

7. An apparatus as in claim 2, in which each photodetector comprises:

a photosensitive element which absorbs light at said respective predetermined wavelength; and a reflector for reflecting light from the light source which has propagated through said plume and the photosensitive element back through the photosensitive element.

8. An apparatus as in claim 7, further comprising a substrate, said reflectors being disposed between said respective photosensitive elements and said substrate, and reflecting substantially all of said unabsorbed light back through said photosensitive elements.

9. An apparatus as in claim 8, in which said photosensitive element is too thin to sense said transmittances without said reflector reflecting said unabsorbed light back through said photosensitive element.

10. An apparatus as in claim 2, in which the photosensor further comprises a homogenizer disposed between said plume and the photosensor for causing said light to be incident on the photodetectors with substantially uniform intensity.

11. An apparatus as in claim 10, in which the light source radiates said light through said plume as a beam.

12. An apparatus as in claim 11, in which the homogenizer comprises a multifaceted optical beam integrator.

13. An apparatus as in claim 1, further comprising:

a video camera for producing a video image of the vehicle; and a combiner for combining said video image from the camera with said composition from the computer.

14. An apparatus as in claim 13, further comprising a video monitor for displaying said video image from the camera and said composition from the computer.

15. An apparatus as in claim 13, further comprising a video recorder for recording said video image from the camera and said composition from the computer.

16. An apparatus as in claim 15, in which the computer controls the video recorder to record said video image from the camera and said composition from the computer only if said composition is outside a predetermined range.

17. An apparatus as in claim 1, in which:

said predetermined wavelengths include spectral absorption peaks of predetermined constituents of said composition;

said predetermined wavelengths further include a predetermined reference wavelength which is not a spectral absorption peak of said predetermined constituents; and the computer computes said transmittances as ratios of transmittances of said predetermined wavelengths which are spectral absorption peaks of said predetermined constituents and a transmittance of said reference wavelength.

18. An apparatus as in claim 17, in which said predetermined constituents comprise nitric oxide and water, said computer compensating the transmittance associated with nitric oxide in accordance with the transmittance of the water.

19. An apparatus as in claim 18, further comprising a calibration cell that is interposed between said photosensor and the plume such that the light passes through said calibration cell, said calibration cell comprising a compartment having a volume that contains NO, water, and at least one combustion product in a predetermined concentration, said calibration cell further including an actuator for controllably varying the volume of said compartment.

20. An apparatus as in claim 19, wherein said predetermined constituents further comprise a hydrocarbon (HC), carbon monoxide (CO) and carbon dioxide ($CO_2$), and said volume further contains HC, CO and $CO_2$.

21. An apparatus as in claim 1, in which said photosensor senses radiation that is emitted by said plume, said computer computing said transmittances from said respective differences results in transmittances that are substantially unaffected by the radiation emitted by said plume.

22. A sensing apparatus for sensing a composition of a fluid, comprising:

a light source for radiating light including a plurality of predetermined wavelengths through said fluid;

a chopper positioned between said source and said fluid for alternating blocking and passing said light;

a photosensor for simultaneously sensing alternating blocked or passed radiation levels at said predetermined wavelengths for said light passing through said fluid; and a computer for computing transmittances of said predetermined wavelengths from respective differences between said blocked and passed radiation levels, and computing said composition as a predetermined function of said transmittances.

23. An apparatus as in claim 22, in which:

the photosensor comprises a plurality of photodetectors, each photodetector being sensitive to a band of wavelengths that includes only one of said predetermined wavelengths; and the photosensor is disposed such that said light from the light source is simultaneously incident on the photodetectors.

24. An apparatus as in claim 23, in which the photosensor further comprises light blocking members for optically isolating the photodetectors from each other.

25. An apparatus as in claim 23, in which the photosensor further comprises a substrate on which the photodetectors are substantially isothermally disposed.

26. An apparatus as in claim 25, in which the photosensor further comprises a temperature regulator for maintaining the substrate and photodetectors at a predetermined temperature.

27. An apparatus as in claim 23, in which each photodetector comprises:

a photosensitive element; and a filter disposed between said fluid and the photosensitive element having a passband coinciding with said respective band of wavelengths.

28. An apparatus as in claim 23, in which each photodetector comprises:

a photosensitive element which absorbs light at said respective predetermined wavelength; and a reflector for reflecting light from the light source which has propagated through said fluid and the photosensitive element back through the photosensitive element.

29. An apparatus as in claim 23, in which the photosensor further comprises a homogenizer disposed between said fluid and the photosensor for causing said light to be incident on the photodetectors with substantially uniform intensity.

30. An apparatus as in claim 29, in which the light source radiates said light through said fluid as a beam.

31. An apparatus as in claim 30, in which the homogenizer comprises a multifaceted optical beam integrator.

32. An apparatus as in claim 22, in which:

said predetermined wavelengths include spectral absorption peaks of predetermined constituents of said fluid;

said predetermined wavelengths further include a predetermined reference wavelength which is not a spectral absorption peak of said predetermined constituents; and the computer computes said transmittances as ratios of transmittances of said predetermined wavelengths which are spectral absorption peaks of said predetermined constituents and a transmittance of said reference wavelength.

33. A system for determining a concentration of nitric oxide (NO) and carbon monoxide (CO) in an exhaust plume that emits radiation, comprising:

a source of electromagnetic radiation for directing radiation having a plurality of wavelengths along an optical path that passes through the plume;

chopper means disposed between said source and said plume for alternately blocking and passing said radiation from said source;

first sensor means having an output for indicating an amount of absorption of the radiation transmitted through said plume from said source and emitted by said plume, within a band of first wavelengths, that is due to the presence of NO in the plume;

second sensor means having an output for indicating an amount of absorption of the radiation, within a band of second wavelengths, that is due to the presence of water along the optical path; and third sensor means having an output for indicating an amount of absorption of the radiation transmitted through said plume from said source and emitted by said plume, within a band of third wavelengths, that is due to the presence of CO in the plume;

determining means, having inputs coupled to the outputs of said first, second and third sensor means, for compensating the indicated absorptions when said chopper means passes said radiation in accordance with the indicated absorptions when said chopper means blocks said radiation to produce respective normalized absorptions, and for further compensating the normalized absorption within the first band of wavelengths in accordance with the normalized absorption within the second band of wavelengths and in accordance with a predetermined NO absorption modifying factor.

34. A system as set forth in claim 33 wherein the predetermined NO absorption modifying factor is stored within a lookup table means.

35. A system as set forth in claim 33 and further comprising:

fourth sensor means having an output for indicating an amount of absorption of the radiation transmitted through said plume from said source and emitted by said plume, within a band of fourth wavelengths, that is due to the presence of a predetermined combustion product in the plume; and wherein said determining means includes means for determining concentrations of NO and CO in the plume from the compensated normalized absorption within the first band of wavelengths and the normalized absorption within the third band of wavelengths, respectively, in accordance with the indication from said output of said fourth sensor means.

36. A system as set forth in claim 35 wherein the predetermined combustion product is $CO_2$.

37. A system as set forth in claim 35 and further comprising a calibration cell that is interposed between said first, second third and fourth sensor means and the plume such that the radiation passes through said calibration cell, said calibration cell comprising a compartment having a volume that contains NO, CO, water, and at least one combustion product in a predetermined concentration, said calibration cell further including means for controllably varying the volume of said compartment.

38. A system as set forth in claim 33 and further comprising:

fifth sensor means having an output for indicating a variation in the intensity of the radiation within a band of fifth wavelengths that are selected so as not to be significantly absorbed within the plume; and wherein said determining means is responsive to said output of said sensor means for compensating the indicated absorptions within the first, second and third bands of wavelengths in accordance with the indication output by said fifth sensor means.

39. A system as set forth in claim 33 wherein said source of electromagnetic radiation outputs radiation within a band of wavelengths that includes a band from approximately 3 microns to approximately 6 microns, said first band of wavelengths includes a wavelength of approximately 5.26 microns, said second band of wavelengths includes a wavelength of approximately 5.02 microns and said third band of wavelengths includes a wavelength of approximately 4.6 microns.

40. A system as set forth in claim 33 wherein said first sensor means includes a first photodetector and a first filter interposed between the first photodetector and the plume, the first filter having a wavelength passband of predetermined width that includes a wavelength of 5.26 microns; said second sensor means includes a second photodetector and a second filter interposed between the second photodetector and the plume, the second filter having a wavelength passband of predetermined width that includes a wavelength of 5.02 microns; and said third sensor means includes a third photodetector and a third filter interposed between the third photodetector and the plume, the third filter having a wavelength passband of predetermined width that includes a wavelength of 4.6 microns.

41. A system as set forth in claim 40 and further comprising means for homogenizing the radiation after the radiation passes through the plume, said homogenizing means being interposed between each of said first, second and third filters and said plume.

42. A method for determining a concentration of nitric oxide (NO) and carbon monoxide (CO) in an exhaust plume that emits radiation, comprising the steps of:

passing an optical beam through an exhaust plume, the optical beam having wavelengths within a predetermined band of wavelengths within the infrared radiation spectrum;

alternately blocking and Unblocking said radiation from said source;

sensing blocked and unblocked radiations levels within said predetermined band;

determining a measured NO transmission value from said blocked and unblocked radiation levels for a first predetermined band of wavelengths;

determining a measured water transmission value from said blocked and unblocked radiation levels for a second predetermined band of wavelengths;

determining a measured reference transmission value from said blocked and unblocked radiation levels for a third predetermined band of wavelengths selected so as not to be significantly absorbed by the exhaust plume;

determining a measured combustion by-product transmission value from said blocked and unblocked radiation levels for a fourth predetermined band of wavelengths;

determining a measured CO transmission value from said blocked and unblocked radiation levels for a fifth predetermined band of wavelengths;.

determining an effective NO transmission value from the measured NO transmission value that is scaled by the (a) measured water transmission value, (b) a predetermined factor that compensates for absorption by water within the first predetermined band of wavelengths, and (c) the reference transmission value;

determining an effective CO transmission value from the measured CO transmission value that is scaled by the reference transmission value;

converting the effective NO and CO transmission values to relative NO and CO concentrations using predetermined calibration factors; and converting the relative NO and CO transmission values to NO and CO concentration values utilizing the measured combustion by-product transmission value.

43. A method as set forth in claim 42 wherein the predetermined combustion by-product is $CO_2$.

44. A method asset forth in claim 42 wherein the exhaust plume is generated by a motor vehicle, and further comprising the steps of:

comparing the NO and CO concentrations to predetermined values; and, if they exceed the predetermined values, recording an identifying characteristic of the motor vehicle in association with the NO and CO concentrations.

45. A method as set forth in claim 42 wherein the step of determining an effective NO transmission value $(T(NO)_{\textit{eff}})$ is accomplished in accordance with:

$$T(NO)_{\textit{eff}} = T(NO)/(T(H_2O) \times \{\text{Lookup } (H_2O \text{ band to NO band})\} \times T(REF)),$$

where, T(NO) is the measured NO transmission value, T($H_2O$) is the measured water transmission value, Lookup ($H_2O$ band to NO band) is a predetermined water/NO absorption correction, and T(REF) is the measured reference transmission value for the third predetermined band of wavelengths.

46. A sensing apparatus for sensing a composition of an exhaust plume of a motor vehicle, comprising:

a light source for radiating light including a plurality of predetermined wavelengths through said plume;

a plurality of photodetectors on a substrate for simultaneously sensing radiation levels at respective ones of said predetermined wavelengths for said light passing through said plume, two of said predetermined wavelengths responding to the presence of nitric oxide and water respectively, each photodetector comprising a photosensitive element which absorbs light at one of said respective predetermined wavelengths and a reflector between said photosensitive element and said substrate for reflecting light from the light source which has propagated through said plume and the photosensitive element back through the photosensitive element; and a computer for computing transmittances of said predetermined wavelengths from said respective radiation levels and computing said composition as a predetermined function of said transmittances, said computer compensating the transmittance associated with nitric oxide in accordance with the transmittance of the water.

47. An apparatus as in claim 46, in which said reflector reflects substantially all of said unabsorbed light back through said photosensitive element.

48. An apparatus as in claim 47, in which said photosensitive element is too thin to sense said transmittances without said reflector reflecting said unabsorbed light back through said photosensitive element.

49. A sensing apparatus for sensing a composition of an exhaust plume of a motor vehicle, comprising:

a light source for radiating light including a plurality of predetermined wavelengths through said plume;

at least three photodetectors for simultaneously sensing radiation levels at respective ones of said predetermined wavelengths for said light passing through said plume, two of said photodetectors responding to the presence of nitric oxide and water respectively;

a homogenizer disposed between said plume and said photosensor for causing said light to be incident onto a continuous area of the photodetectors with substantially uniform intensity to reduce the spatial variance of said sensed radiation levels; and a computer for computing transmittances of said predetermined wavelengths from said respective radiation levels and computing said composition as a predetermined function of said transmittances said computer compensating the transmittance associated with nitric oxide in accordance with the transmittance of the water.

50. A sensing apparatus for sensing a composition of an exhaust plume of a motor vehicle comprising:

a light source for radiating light including a plurality of predetermined wavelengths through said plume as a beam;

at least three photodetectors for simultaneously sensing radiation levels at respective ones of said predetermined wavelengths for said light passing through said plume:

a homogenizer disposed between said plume and said photosensor for causing said light to be incident onto a continuous area of the photodetectors with substantially uniform intensity to reduce the spatial variance of said sensed radiation levels, said homogenizer comprising a multifaceted optical beam integrator that images respective segments of said beam onto a series of overlapping segments on said photodetectors; and a computer for computing transmittances of said predetermined wavelengths from said respective radiation levels and computing said composition as a predetermined function of said transmittances.

* * * * *